United States Patent
Moreau (10) Patent No.: US 8,149,991 B2
(45) Date of Patent: Apr. 3, 2012

(54) TREATMENT OPTIMIZATION

(75) Inventor: Michel Moreau, Verona, WI (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 164 days.

(21) Appl. No.: 12/531,492

(22) PCT Filed: Mar. 6, 2008

(86) PCT No.: PCT/IB2008/050828
§ 371 (c)(1),
(2), (4) Date: Sep. 16, 2009

(87) PCT Pub. No.: WO2008/114159
PCT Pub. Date: Sep. 25, 2008

(65) Prior Publication Data
US 2010/0046706 A1 Feb. 25, 2010

Related U.S. Application Data (60) Provisional application No. 60/895,488, filed on Mar. 19, 2007.

(51) Int. Cl.
*A61B 6/03* (2006.01)
*A61B 5/05* (2006.01)
*A61N 5/10* (2006.01)
*A61N 5/00* (2006.01)

(52) U.S. Cl. .......................... 378/65; 600/427; 600/429

(58) Field of Classification Search ............... 378/65, 378/147–152; 128/922; 600/407, 427–429, 600/1, 2
See application file for complete search history.

(56) References Cited

U.S. PATENT DOCUMENTS

| | | | |
|---|---|---|---|
| 3,248,547 A * | 4/1966 | Van De Geijn | 378/157 |
| 5,647,663 A | 7/1997 | Holmes | |
| 6,393,096 B1 * | 5/2002 | Carol et al. | 378/65 |
| 6,661,871 B2 | 12/2003 | Siochi | |
| 6,853,705 B2 | 2/2005 | Chang | |
| 2003/0219098 A1 * | 11/2003 | McNutt et al. | 378/65 |
| 2004/0071261 A1 | 4/2004 | Earl et al. | |
| 2004/0213381 A1 * | 10/2004 | Harada | 378/152 |
| 2006/0045238 A1 | 3/2006 | Nguyen | |
| 2008/0031406 A1 * | 2/2008 | Yan et al. | 378/14 |

FOREIGN PATENT DOCUMENTS

| | | |
|---|---|---|
| WO | 03076003 A2 | 9/2003 |
| WO | 2005062790 A2 | 7/2005 |
| WO | 2006039591 A2 | 4/2006 |

OTHER PUBLICATIONS

Yu, Intensity-modulated arc therapy with dynamic multileaf collimation: an alternative to tomotherapy, Phys. Med.Biol., Apr. 20, 1995, pp. 1435-1449, vol. 40, IOP Publishing Ltd.

Gill, et al., User's Guide for NPSOL 5.0: A Fortran Package for Nonlinear Programming, Jul. 30, 1998, 46 pages.

(Continued)

*Primary Examiner* — Anastasia Midkiff (57) ABSTRACT

A treatment planning and delivery system includes a treatment planner (102) and a treatment device (104). The treatment planner (102) develops a treatment plan that satisfies one or more of treatment objectives (122), treatment device output objectives (124), and treatment device parameter objectives (126). The treatment plan is applied by the treatment device (104), Examples of treatment device output and treatment device parameter objectives include spatial and temporal objectives.

11 Claims, 5 Drawing Sheets

OTHER PUBLICATIONS

Galvin, The Multileaf Collimator—A Complete Guide, 1999 Annual Meeting of the American Association of Physicists in Medicine handout, Jul. 28, 1999, pp. 1-17, http//www.aapm.org/meetings/99AM/pfd/2787-9625.pdf.

Wu, et al. Algorithms and functionality of an intensity modulated radiotherapy optimization system, Medical Physics, Apr. 2000, pp. 701-711, vol. 27, No. 4.

Spirou, et al., Smoothing intensity-modulated beam profiles to improve the efficiency of delivery, Medical Physics, Oct. 2001, pp. 2105-2112, vol. 28, No. 10.

Yu, et al., Clinical Implementation of Intensity-Modulated Arc Therapy, Int. J. Radiation Oncology Biol. Phys., 2002, pp. 453-463, vol. 53, No. 2.

Lof, et al., P3IMRT Inverse planning optimization, Pinnacle 3 White Paper, 2003, pp. 1-4, Royal Philips Electronics.

Hardemark, et al., P3IMRT Direct machine parameter optimization, Pinnacle 3 White Paper, 2004, pp. 1-8, Royal Plilips Electronics.

Yu, Modulated Radiotherapy—Current Status and New Developments, Business Briefing: US Oncology Review, 2006, reference section pp. 1-4.

Varian Medical Systems, The Advantages of Millennium Multileaf Technology, published on or before download date Feb. 21, 2007, 2 pages, http://www.varian.com/orad/prd056.html.

Welsh Cancer Center, Sheridan Memorial Hospital, Multileaf Collimator (MLC), published on or before download date Feb. 21, 2007, 2 pages, http://welchcancercenter.org/Radiation%20Therapy%20Equip/multil. . . .

Radionics, Radionics XKnife MMCL, published on or before download date Feb. 21, 2007, 2 pages, http://www.radionics.com/products/rt/mmIc/shtml.

Beaulieu, F., et al.; Simultaneous optimization of beam orientations, wedge filters and field weights for inverse planning with anatomy-based MLC fields; 2004; Med. Phys.; 31(6)1546-1557.

* cited by examiner

TREATMENT OPTIMIZATION

CROSS REFERENCE TO RELATED APPLICATIONS

This application claims the benefit of U.S. provisional application Ser. No. 60/895,488 filed Mar. 19, 2007, which is incorporated herein by reference.

The present application relates to treatment and treatment planning. While it finds particular application to radiation therapy in medicine, it also relates to other medical and non-medical applications in which it is desired to apply a desired treatment to a patient or other object.

Radiation therapy is an important tool in the treatment of diseases such as cancer. The objective of such a treatment is to induce necrosis in or otherwise retard the growth of a tumor or other lesion, while minimizing the undesirable effects of the treatment on healthy tissues. More specifically, it is generally desirable to apply a relatively high radiation dose to the tumor or lesion while minimizing the dose applied to surrounding risk organs or otherwise healthy tissues.

Due to its ability to produce and deliver relatively conformal dose distributions, intensity modulated radiation therapy (IMRT) has gained widespread acceptance as a treatment technique. IMRT treatment plans are often designed using an inverse planning process, which begins by specifying a desired dose to be applied to the lesion or other target, as well as dose limits to risk organs or other critical structures. The treatment is applied using a treatment device such as a linear accelerator and a multi-leaf collimator or compensator. In a variant that is sometimes referred to as forward planning, the user specifies certain system settings, and the system optimizes others. When planning treatments for breast tumors, for example, the user may establish desired collimator leaf positions (i.e., the segment shapes), and the planning system optimizes the relative weights of the various segments. More recently, treatment techniques such as intensity modulated arc therapy (IMAT) and so-called tomotherapy have been developed. These systems typically vary the intensity of the applied radiation as relative positions of the radiation beam and the patient are varied.

While IMRT, IMAT, and tomotherapy systems represent an important advance in medical treatment, there nonetheless remains room for improvement.

Aspects of the present application address these matters and others.

In accordance with one aspect, an apparatus plans a treatment that includes the spatially varying application of energy to an object by a treatment device. The apparatus includes a treatment planner that optimizes a characteristic of the treatment according to a treatment objective and a parameter of the treatment device according to a treatment device parameter objective.

According to another aspect, a method of planning a treatment that includes the application of energy to a target of an object by a treatment device includes the steps of optimizing a treatment plan according to a treatment objective and a treatment device parameter objective and making the optimized treatment plan available to the treatment device.

According to another aspect, a computer readable storage medium contains instructions which, when executed by a processor, cause the processor to carry out a method. The method includes generating a treatment plan using a planning method that optimally satisfies a treatment objective and a treatment device parameter objective. The treatment objective includes a spatially varying application of an energy to an object. The method also includes storing the treatment plan in a computer readable memory.

According to another aspect, a method includes receiving an input that describes a desired output of a radiation treatment device and converting the desired output to treatment device parameters that produce the desired output. The treatment device parameters include modulator parameters and the step of converting includes optimizing an objective function that considers a modulator parameter objective.

According to another aspect, a radiation treatment apparatus includes a radiation source, a modulator that modulates a radiation beam produced by the radiation treatment apparatus, and a positioner that positions the beam relative to an object to be treated. The radiation treatment apparatus delivers the beam according to a treatment plan that optimally satisfies a treatment objective and a modulator parameter objective.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
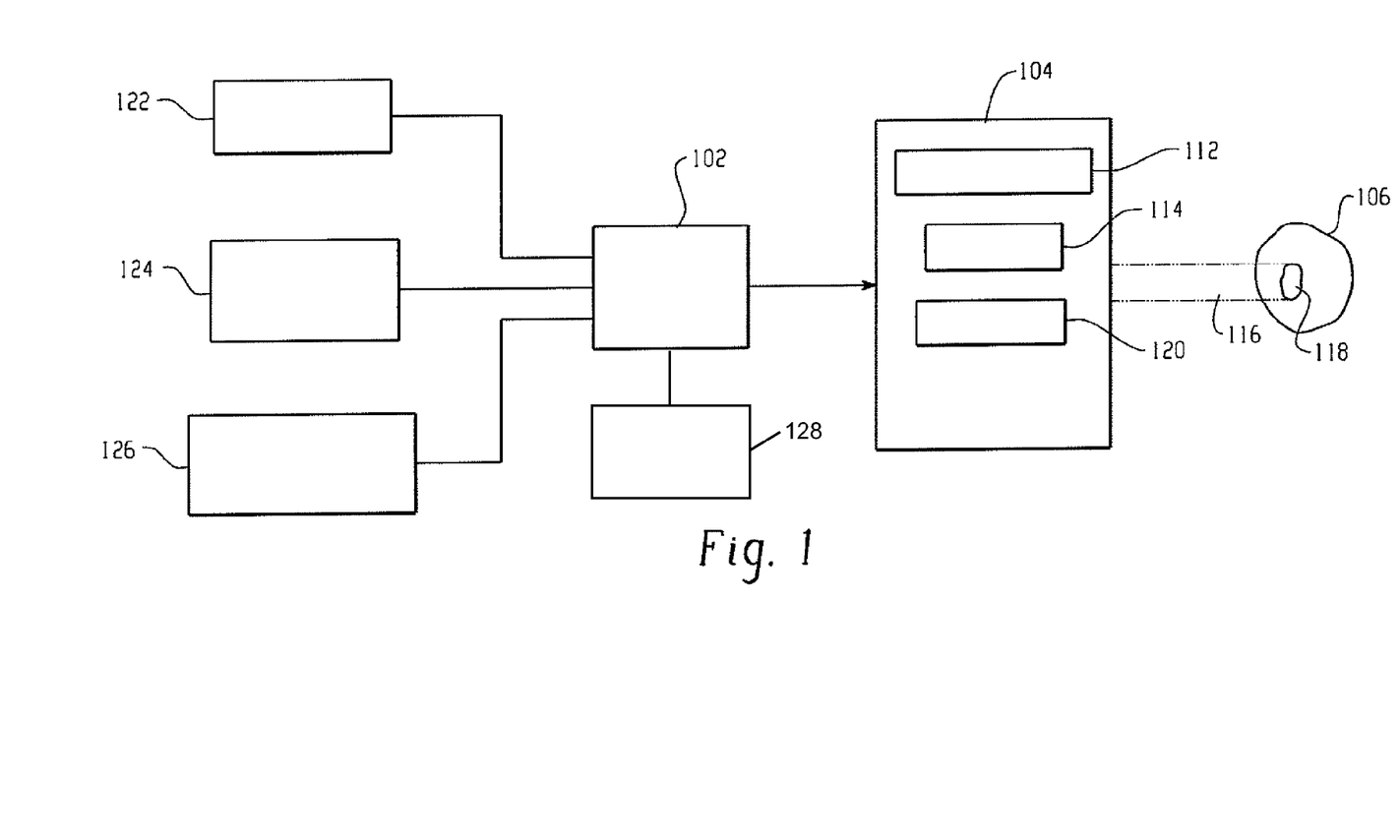
FIG. 1 depicts a treatment planning and delivery system.

With reference to FIG. 1, a treatment planner 102 develops a treatment plan that optimally satisfies one or more of clinical or treatment objectives 122, treatment delivery system output objectives 124, and treatment delivery system parameter objectives 126. A treatment delivery device 104 applies the planned treatment to a patient or other object 106 to be treated.

As illustrated in FIG. 1, the treatment device 104 includes an energy source 112, a modulator 114, and a positioner 120. The energy source 112 produces an energy to be applied to the object 106. Where the treatment device 104 applies a radiation treatment, for example, the energy source 112 may include a linear accelerator, a radioactive material, a particle radiation source (e.g., a proton source), or other source of ionizing radiation.

The modulator 114 modulates the radiation produced by radiation source 112 to generate a spatially varying energy or energy beam 116 that is applied to the object 106. Thus, for example, the shape of the beam 116 may be varied to conform generally to the shape of a tumor or other target 118 when viewed along the direction of the beam 116 (i.e., along a beam's eye view). The modulator 114 may also be configured to adjust the relative spatial intensity or flux of the beam 116 so that relatively higher (or lower) energy doses may be applied to different regions of the target 118.

Again in the case of a treatment device 104 that applies a radiation treatment, examples of suitable modulators 114 include multi-leaf collimators (MLCs) and compensators. A multi-leaf collimator typically includes a plurality of moveable, radiation attenuative leaves interposed between the radiation source 112 and the object 106, with the position of the leaves being varied to produce the desired beam shape and/or spatial intensity profile. A compensator typically includes a radiation attenuative material interposed between the source 112 and the object 106. The material composition and/or thickness profile of the compensator is established to produce the desired beam shape and/or spatial intensity profile, and the compensator is fabricated accordingly.

A positioner 120 varies the relative positions of the energy 116 and the object 106 so that the energy 116 may be applied to the target 118 from one or more different directions. In the case of a treatment device 104 that operates in a static mode, the treatment device 104 and object 106 are positioned so that the energy 116 is applied to the target 118 from a desired direction. The modulator 116 is adjusted to provide a beam shape and/or intensity profile corresponding to the direction, for example by adjusting the positions of the MLC leaves (also known as the step-and-shoot technique) or inserting a compensator having a desired profile. The energy 116 is applied from the desired direction. To aid in the delivery of a spatially varying dose profile, the energy 116 may be delivered in a plurality of segments, with the position of the MLC leaves being adjusted between the various segments. The process is repeated for each of a plurality of directions or positions.

In the case of a treatment device 104 that applies a dynamically varying treatment, the beam 116 traverses one or more arcs or other trajectories relative to the target 118. The beam 116 is applied to the patient 106 temporally concurrently with the relative motion of the beam 116 and the object 106. The modulator 114 is adjusted in coordination with the relative motion so that the desired beam shape and/or intensity profile are applied as the relative motion of the beam and the object changes 118. Examples of dynamically varying treatment techniques used in radiation therapy include intensity modulated arc therapy (IMAT), tomotherapy, and sliding window. In a system that delivers tomotherapy treatments, the beam 116 and patient 106 are moved relative to each other in a trajectory similar to that employed in a computed tomography (CT) system (e.g., in a axial or helical trajectory), with the modulator 114 again being adjusted in coordination with the beam 116 trajectory. In the case of a treatment device that applies the sliding window technique, the direction of the beam 116 is held constant while the MLC leaves are swept across the field during the application of the treatment so as to vary the dose applied to various regions of the patient 106 and/or target 118.

As noted above, the treatment planner 102 plans the treatment to be applied by the treatment device 104. More particularly, the treatment planner 102 is configured as an inverse planning system that seeks a treatment plan that optimally satisfies objectives such as one or more of the clinical or treatment objective(s) 122, the treatment device output objective(s) 124, and the treatment device parameter objective(s) 126.

The treatment objective(s) 122, which describe desired spatially varying treatment objective(s) to be applied to the object 106, are typically entered or confirmed by a clinician or other human user using a user interface 128, such as a computer-implemented graphical user interface (GUI) or other suitable operator interface. Again in the example of radiation therapy, treatment objectives 122 may include one or more of the number and orientation of the radiation or radiation beams 116 to be applied to the target 118, desired beam 116 trajectory(ies), a minimum radiation dose to be applied in the target region 118, a maximum dose to be applied to a region outside the target 118 (e.g., to a risk organ or otherwise healthy tissue), minimum and maximum dose-volume objectives, dose uniformity objectives, and the like.

Multiple maxima, minima, or other objectives may be provided. For example, a first minimum dose objective may be established for a first region or volume of the target 118 and a second minimum dose objective established for a second region (or a sub-region) of the target 118. The various treatment objectives 122 may be weighted according to weight parameters to reflect their relative importance; a treatment objective weight $w_1$ may also be provided to reflect the importance of (or stated conversely, to penalize) the treatment objective(s) 122 relative to the treatment device output objectives 124 and/or treatment device parameter 126 objective(s). Desired treatment constraints may also be provided, for example where the dose applied to a particular region must not exceed a certain value.

The treatment device parameter objective(s) 126 describe desired operating parameter(s) or setting(s) of the treatment device 104. Examples of treatment device objectives 126 include treatment device parameter spatial objectives, treatment device parameter temporal objectives, and treatment device energy objective(s). Spatial objectives may include the spatial smoothness or uniformity of the modulator 114 settings or profiles, as well as other spatial objectives. Temporal objectives may include a time rate of change or temporal uniformity of changes in the modulator 114 settings, as well as other time varying objectives. In the case of a treatment device 104 having an adjustable energy 116, the energy objectives may include a desired energy setting.

Multiple maxima, minima, or other objectives may be provided. The various treatment device parameter objectives 126 may be weighted according to weight parameters to reflect their relative importance; a treatment device parameter objective weight $w_{ts}$ may also be provided to reflect the importance of the treatment device parameter objective(s) 126 relative to the treatment device output objectives 124 and/or treatment 122 objective(s). Desired treatment device constraints may also be provided. Note that the treatment device objectives 126 may be established or preset based on the characteristics of the treatment device 104 and confirmed or changed as necessary by the clinician or other use via the operator interface.

The treatment device output objective(s) 124 describe desired characteristic(s) of the energy 116 produced by the treatment device 104. Examples of treatment device output objectives include output spatial objectives, output temporal objectives, and output energy objectives. Output spatial objectives may include the spatial smoothness of the beam 116 shape, the spatial smoothness of the beam 116 intensity, a desired shape or contour of the beam 116, an arc or trajectory to be traced by the energy 116, or other spatial objectives. Output temporal objectives may include a maximum time rate of change of the beam 116 spatial shape, a maximum time rate of change of the beam 116 spatial intensity, at maximum time rate of change of the beam 116 position, or other objectives which describe an output of the treatment device 104 as a function of time.

Multiple maxima, minima, or other objectives may be provided. The various treatment device output objectives 124 may be weighted according to weight parameters to reflect their relative importance; a treatment device output objective weight $w_o$ may also be provided to reflect the importance of the treatment device output objective(s) 124 relative to the treatment device parameter objectives 126 and/or treatment 122 objective(s). Desired output constraints may also be provided. Note that the output objectives 124 may be established or preset based on the characteristics of the treatment device 104 and confirmed or changed as necessary by the clinician or other use via the operator interface.

Figure 2:
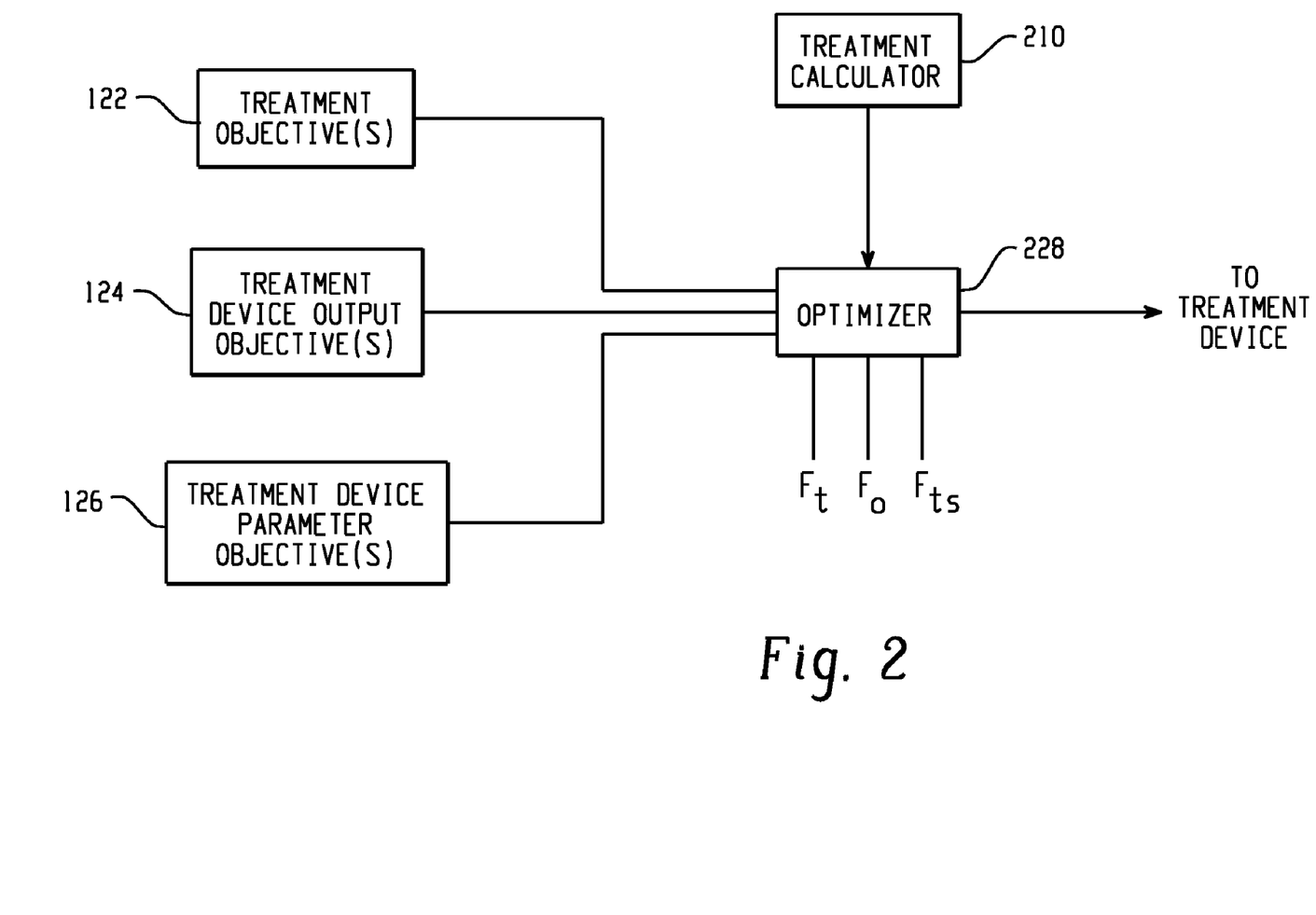
FIG. 2 depicts a treatment planner.

A first embodiment of the treatment planner 102 will now be described with reference to FIG. 2. As illustrated, an optimizer 228 seeks to generate treatment device 104 parameters that optimally satisfy the objectives 122, 124, 126. The optimizer 228 executes an iterative or other optimization algorithm that operates in conjunction with one or more of treatment objective function(s) $F_t$, treatment device output objective function(s) $F_o$, and treatment device parameter objective function(s) $F_{ts}$ and a treatment calculator 210 (e.g., a dose calculation engine in the case of a radiation treatment device). One suitable optimization algorithm utilizes NPSOL, a sequential quadratic programming (SQP) algorithm for solving general nonlinear optimization problems available from Stanford Business Software, Inc. of Palo Alto, Calif. (www.s-b-s-i.com), although other optimization techniques may be selected based on application specific requirements. Note that the optimization may also be performed other than iteratively, for example by suitable direct optimization techniques.

The optimizer 228 seeks to generate treatment device 104 parameters that optimize (e.g., by minimizing or maximizing) an objective function $F_{obj}$ that considers the treatment, treatment device output, and treatment device parameter objectives:

$$F_{obj}=w_tF_t(\text{vol})+w_oF_o(\text{output variables})+w_{ts}F_{ts}(\text{treatment device parameters}) \quad \text{Equation 1}$$

where $F_t(\text{vol})$ is a treatment objective function, $w_t$ is a weight or relative importance to be applied to the treatment objective function, vol represents a target, risk organ, or other volume of the object 106 over which a treatment is to be optimized, $F_o$ represents the output objective function, $w_o$ is a weight or relative importance to be applied to the output objective function, output variable(s) represents the output variables to be optimized, $F_{ts}$ represents the treatment device parameter objective function, $w_{ts}$ is a weight or relative importance to be applied to the treatment device parameter objective function, and treatment device parameter(s) represents the treatment device 104 parameters to be optimized. Note that additional terms may be provided to represent additional treatment, output, or treatment device objectives; one or more of the terms may also be omitted.

Figure 3:
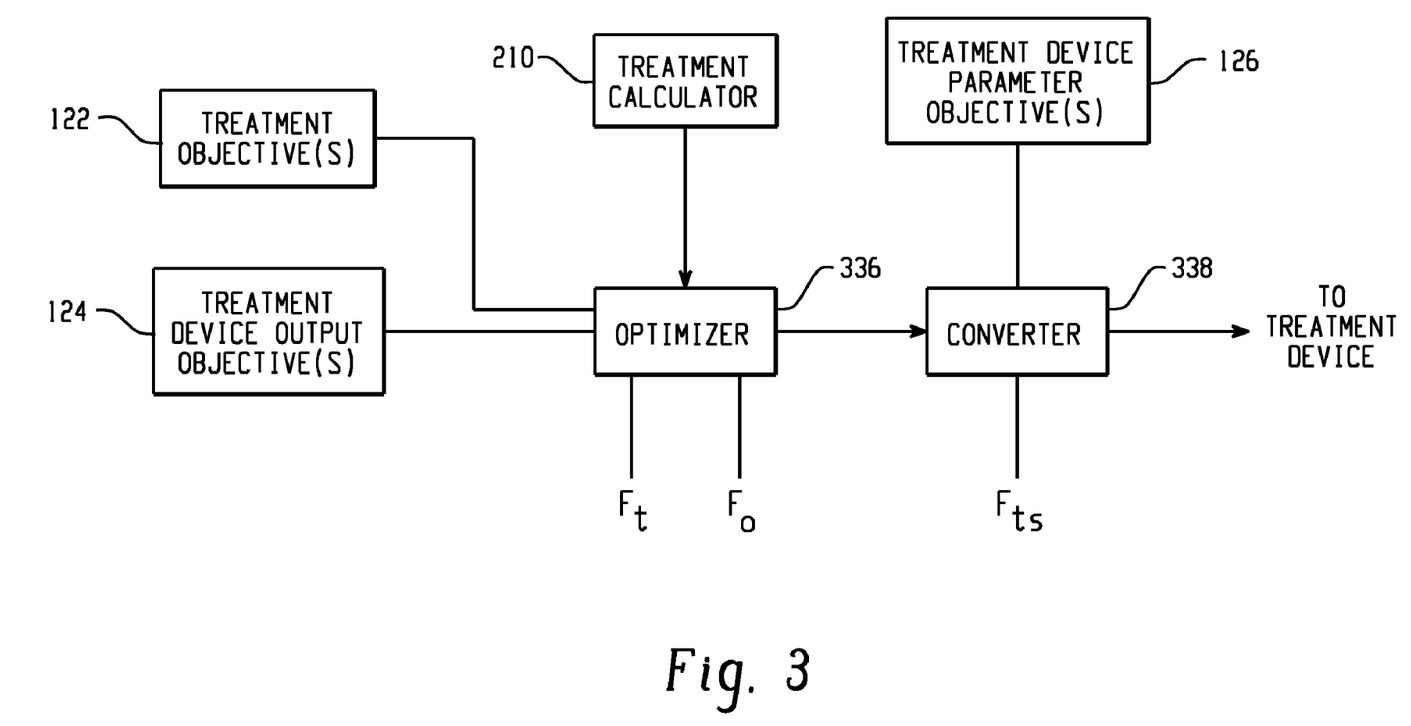
FIG. 3 depicts a treatment planner.

A second embodiment of the treatment planner 102 will now be described in relation to FIG. 3. As illustrated, the treatment planner 102 includes an optimizer 336 and a converter 338. The optimizer 336 seeks to generate a treatment device output that optimally satisfies the treatment 122 and treatment device output 124 objectives:

$$F_{obj}=w_tF_t(\text{vol})+w_oF_o(\text{output variables}). \quad \text{Equation 2}$$

The converter 338 converts the desired output to treatment device parameters that produce the desired treatment device output, for example by optimizing an objective function of the form:

$$F_{obj}=w_oF_o(\text{output variables})+w_{ts}F_{ts}(\text{treatment device parameters}) \quad \text{Equation 3}$$

Note that the functions of the optimizer 336 and converter 338 may be performed successively using a common optimization algorithm.

The foregoing techniques will now be illustrated in connection with an IMRT application in which the spatial irregularities in the attenuation values of a compensator are reduced or otherwise minimized. An objective function that considers a treatment objective and compensator parameter objective may be expressed as follows:

$$F_{obj}=w_1f_1(D_{ijk})+w_2f_2(t_{uv}). \quad \text{Equation 4}$$

The first term represents a conventional IMRT treatment objective function, where $D_{ijk}$ is the dose distribution inside the object, $f_1(D_{ijk})$ is a function that seeks to produce the desired dose distribution in the object 106, and $w_1$ is a desired weight or relative importance to be applied to the treatment objective. The second term represents a function that seeks to minimize local differences in thickness in areas or regions of the compensator, where $t_{uv}$ is the thickness of the compensator at compensator pixels u, v, $f_2(t_{uv})$ is a function that seeks to reduce the local variations in thickness of the compensator, and $w_2$ is a desired weight or relative importance. While omitted from Equation 6, a term representative of the treatment device 104 output may also be included.

Figure 4:
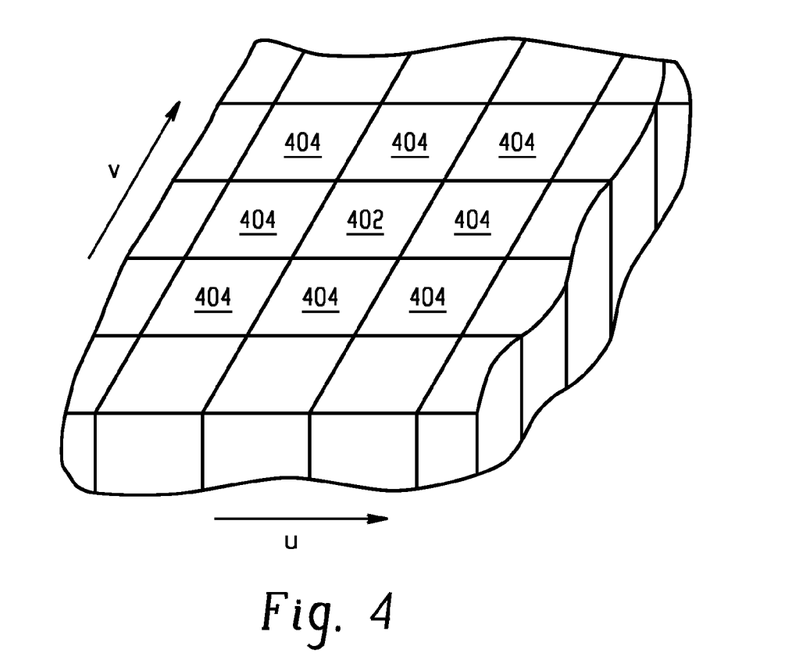
FIG. 4 is a perspective view of a compensator.

Various thickness functions $f_2(t_{uv})$ are contemplated. FIG. 4 depicts a function that seeks to minimize thickness variations in 3×3 groups of compensator pixels that include a reference pixel 402 and its first order or nearest neighbors 404, where the objective is to reduce the standard deviation, gradient or other measure of the variation in thickness of the pixels in the group. Second or higher order neighbors may also be considered, as may second or higher order compensator thickness variations such as the variance. In order to allow the compensator to accommodate relatively sharp gradients in the desired dose distribution, the function $f_2$ should allow a specified number or fraction of the compensator pixels to violate the objective without or at a reduced penalty.

An objective function that considers the treatment objective, the output of a treatment device 104 that includes an MLC, as well as the MLC settings, may be expressed as follows:

$$F_{obj}=w_1f_1(D_{ijk})+w_3f_3(\psi_{uv})+w_4f_4(x_{lsb}). \quad \text{Equation 5}$$

In Equation 7, the second term represents a function that seeks to minimize spatial variations in the radiation beam 116, where $\psi_{uv}$ represents the beam 116 flux at beam pixels u, v and $f_3(\psi_{uv})$ is a function that seeks to reduce variations in the beam 116 flux. The third term represents a function that seeks to optimize the MLC aperture shape, where $x_{lsb}$ represents the position of the MLC leaf l in segment s for beam b, $f_4(x_{lsb})$ is a function that seeks to improve or otherwise maximize the spatial smoothness of the MLC aperture, and b represents the various directions from which the beam 116 is to be applied.

Figure 5:
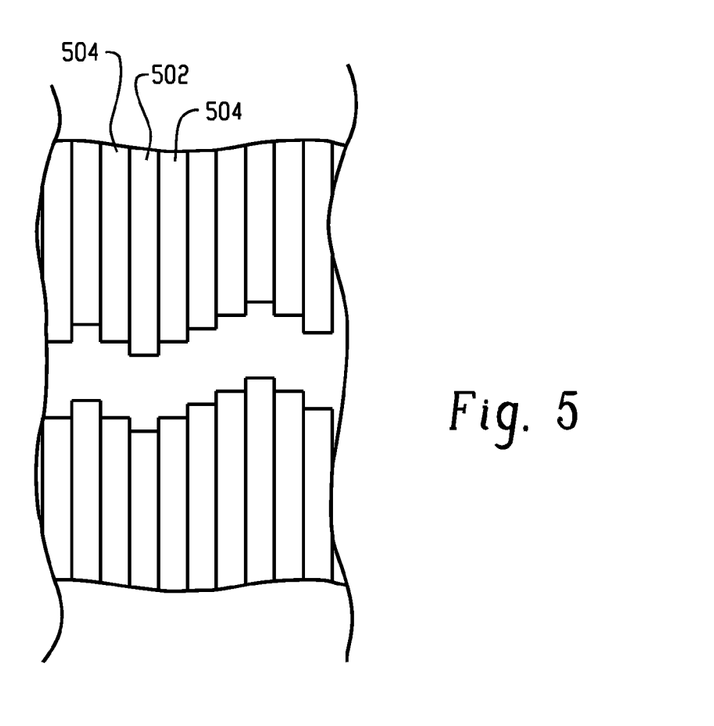
FIG. 5 depicts a multi-leaf collimator.

Various aperture optimization functions are contemplated. FIG. 5 depicts a function that seeks to minimize the difference between the position of the adjacent leaves, in the case of a reference leaf 502 and its first order or nearest neighbors 504. Second or higher order neighbors may also be considered. Higher order spatial functions (e.g., spatial acceleration) may also be considered. In order to allow the MLC to accommodate relatively sharp gradients in the desired dose distribution, the function $f_4(x_{lsb})$ should allow a specified number or fraction of the leaf positions to violate the objective without or at a reduced penalty.

An optimization function that considers the time rate of change of both the treatment device output and the aperture shape can be expressed as follows:

$$F_{obj}=w_1f_1(D_{ijk})+w_5f_5(\psi'_{uv})+w_6f_6(x'_{lsb}). \quad \text{Equation 6}$$

In Equation 8, the second term represents a function that seeks to minimize the time rate of change of the intensity of the radiation beam 116, where $\psi'_{uv}$ represents the rate of change of the beam 116 flux at beam pixels u, v and $f_5(\psi'_{uv})$ is a function that seeks to minimize the time rate of change of the beam 116 flux. The third term represents a function that seeks to reduce the time rate of change of the MLC leaf settings, where $X'_{lsb}$ represents the speed of the MLC leaves and $f_6(x'_{lsb})$ is a function that seeks to reduce the rate of motion.

It will also be appreciated that a given objective function may include both spatial and time varying objectives. Energy or other objectives may also be considered. Those of ordinary skill in the art will also appreciate that the various techniques may also be applied to the embodiment of FIG. 3 and Equations 4 and 5.

Spatial treatment device parameter objectives 126 are particularly useful where the treatment is affected by the spatial characteristics of the treatment device 104. In radiation treatment implementations, for example, minimizing spatial variations in the modulator 114 settings can in some cases improve the accuracy of the dose computed by the planning system. A radiation source 114 such as a linear accelerator may produce scatter radiation that does not emanate from the accelerator's focal spot. While the scatter radiation can account for a significant portion of the overall dose, its contribution can be relatively difficult to model, especially where the spatial variations in the modulator 114 settings are relatively large. In the case of a compensator, minimizing or otherwise controlling thickness variations may also simplify the machining process. In the case of an MLC, minimizing the variation in or controlling the leaf positions may likewise simplify the positioning requirements. While consideration of the treatment device output parameters 124 can ordinarily be expected to result in more readily achievable modulator 114 settings, consideration of the treatment device output parameters may be omitted.

Temporally varying treatment device parameter objectives are particularly useful where the treatment is affected by the temporal characteristics of the treatment device 102. In IMAT and other treatment techniques in which the beam 116 is dynamically modulated as the relative positions of beam 116 and object 106 are varied, for example, the rate at which the relative positions of the beam 116 and the object 106 can be varied may be limited by the rate at which the modulator 114 can be adjusted. In such cases, treatment plans in which the rate of change of the modulator 114 settings is relatively reduced may be expected to reduce treatment times or otherwise simplify the modulator positioning requirements. While consideration of temporally varying treatment device output parameters can likewise be expected to require more readily achievable modulation rates, consideration of the treatment device output temporal parameters may be omitted.

Other therapy systems are contemplated. Examples include systems that apply radio frequency, thermal, sonic, or other energy to the target 118. Depending on the nature of the energy source 112, the modulator 114 may take other forms. The modulator 114 may also control or adjust the operation of the energy source 102, for example where the energy source 112 includes a phased array transducer. While the above description has also focused on dose-based treatment functions, other functions, such as functions that describe the biological response of tumors or other tissues to the applied treatment, may also be used.

The treatment planner 102 may be implemented by way of computer readable instructions stored in suitable computer readable media. When executed by a computer processor or processors, the instructions cause the processor to carry out the described functions. It should also be noted that the treatment planning and the application of the treatment need not be performed physically or temporally concurrently. Thus, the planner 102 and treatment device 104 may be located remotely from one another and communicate over a suitable communications network. The treatment planning may likewise be performed in advance of the arrival of the object 106 at the treatment device 104.

Figure 6:
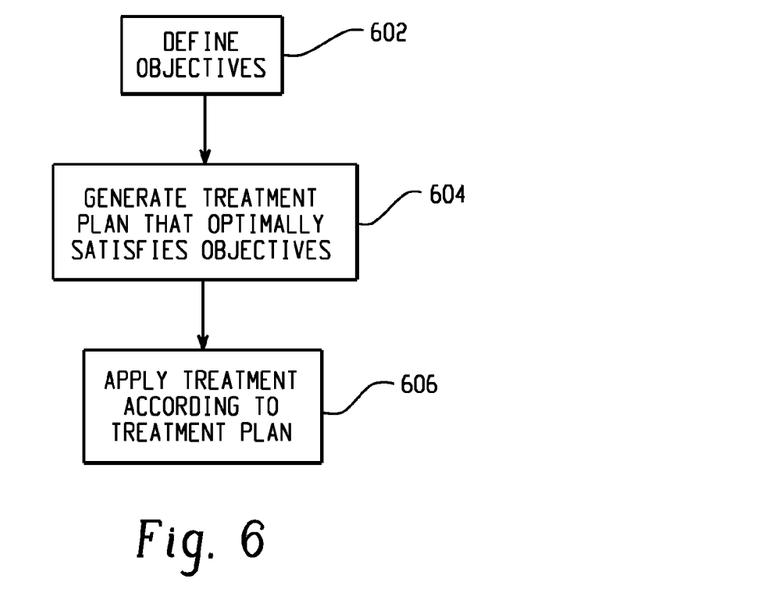
FIG. 6 depicts a method.

Operation will now be described with reference to FIG. 6. The desired objectives are defined at 602. As noted above, for example, the objectives may include one or more of treatment objectives 122, treatment device output objectives 124, treatment device parameter objectives 126, or other objectives. The objectives may also include desired weights.

A treatment plan that optimally satisfies the objectives is developed at 604. This may be accomplished, for example, using an iterative optimization algorithm that considers the relevant objectives as part of the optimization process.

At 606, the treatment is applied according to the treatment plan.

Figure 7:
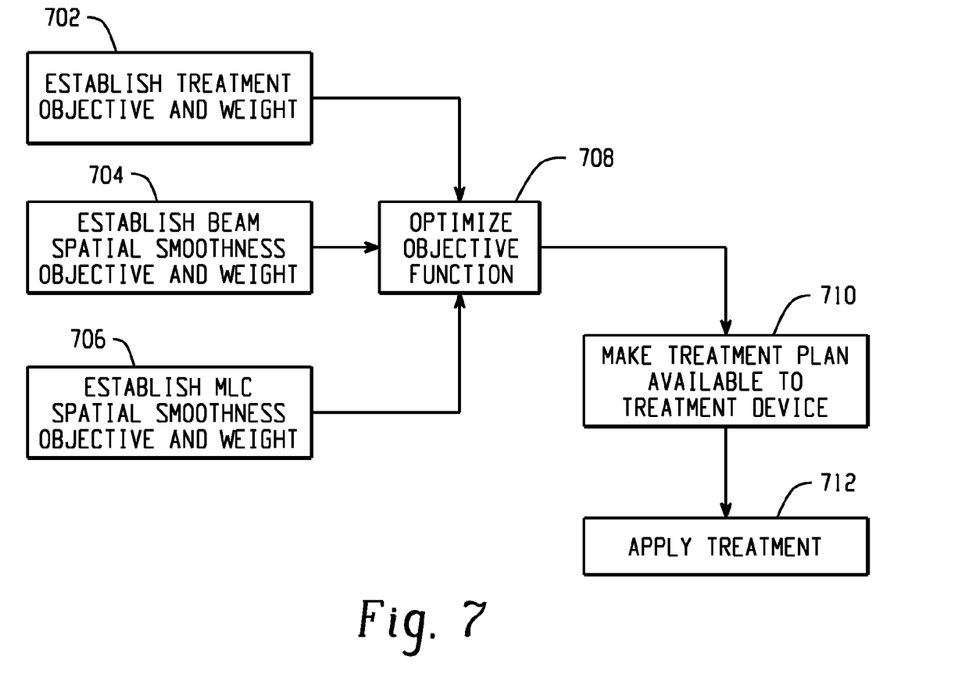
FIG. 7 depicts a method.

FIG. 7 further illustrates a radiation treatment system that includes optimization of a treatment objective, a beam spatial smoothness objective, and an MLC spatial smoothness according to the optimization function of Equation 1.

Treatment objective(s) and weight(s) are established at 702, beam spatial smoothness objective(s) and weight(s) are established at 704, and MLC spatial smoothness objective(s) and weight(s) are established at 706. In the case of the treatment of a tumor in radiation oncology, for example, a clinician or other user may wish to establish one or more dose objectives for various regions of the target 118 and/or object 106.

The spatial smoothness objectives represent a desired spatial smoothness of the radiation beam 116 produced by the treatment device 104 and the spatial smoothness of the MLC leaves, respectively. The weights represent the relative importance of the various objectives. By way of one example, a user may determine that the dose objective is relatively more important than the spatial smoothness objectives. Conversely, the user may decide that the spatial smoothness of the MLC settings is relatively more important, in which case these settings may be weighted relatively more heavily.

At 708, an objective function such as the one described above in connection with Equation 1 is used to produce treatment parameter(s) that optimally satisfy the desired objectives and weights. If the user has assigned a relatively higher importance to the dose objective than to the MLC spatial smoothness objective, for example, the treatment plan may produce MLC settings with a relatively higher degree of spatial irregularity. By increasing the weight applied to the MLC objective, however, the spatial smoothness would be expected to play a relatively greater role in the optimization process.

At 710, the treatment plan is made available to the treatment device 104.

At 712, the treatment is applied to the object 106.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of planning a treatment that includes the application of energy to a target of an object by a treatment device, the method comprising:
    optimizing a treatment plan according to a treatment objective and a treatment device parameter objective, wherein the treatment objective and treatment device parameter objective are weighted against one another according to a user-defined weighting that is used in optimizing the treatment plan;
    making the optimized treatment plan available to the treatment device.

2. The method of claim 1 wherein the treatment objective includes a first dose objective for the target and a second dose objective for a healthy tissue of the object.

3. The method of claim 1 wherein the treatment device includes a modulator that modulates an output of the treatment device and the treatment device parameter objective includes a modulator uniformity objective.

4. The method of claim 1 wherein optimizing includes optimizing a treatment device setting according to the treatment device parameter objective.

5. The method of claim 1 wherein optimizing includes optimizing an objective function that considers both the treatment objective and the treatment device parameter objective.

6. The method of claim 1 wherein optimizing includes
optimizing a first objective function that considers the treatment objective;
optimizing a second objective function that considers the treatment device parameter objective.

7. A computer readable storage medium containing instructions which, when executed by a processor, cause the processor to carry out a method that comprises:
generating a treatment plan using an planning method that optimally satisfies a weighted first treatment objective, a weighted second treatment objective, a weighted first treatment device parameter objective, and a weighted second treatment device parameter objective, wherein the first weighted treatment objective includes a spatially varying application of an energy to an object, wherein the weighted first treatment objective is weighted against the weighted second treatment objective and wherein the weighted first treatment device parameter objective is weighted against the weighted second treatment device parameter objective;
storing the treatment plan in a computer readable memory.

8. The computer readable storage medium of claim 7 wherein the treatment device includes an aperture and the weighted first treatment device parameter objective includes a spatial characteristic of the aperture.

9. The computer readable storage medium of claim 7 wherein the treatment device includes a collimator that includes a plurality of leaves and the method includes generating a measure of a variation in the positions of a leaf and its first order neighbors.

10. The computer readable storage medium of claim 7 wherein the treatment device includes a compensator that provides a spatially varying attenuation and the method includes generating a measure of a difference in attenuation of the compensator in first and second spatial dimensions.

11. The computer readable storage medium of claim 7 wherein the treatment device includes a modulator and generating includes:
generating a desired treatment device output;
converting the treatment device output to a modulator parameter.

* * * * *